United States Patent [19]
Murray

[11] Patent Number: 5,380,869
[45] Date of Patent: Jan. 10, 1995

[54] REGIOSELECTIVE SYNTHESIS OF 1,5-DIARYL PYRAZOLE ANTI-INFLAMMATORY AGENTS

[75] Inventor: William V. Murray, Belle Mead, N.J.

[73] Assignee: Ortho Pharmaceutical Corporation, Raritan, N.J.

[21] Appl. No.: 113,484

[22] Filed: Aug. 27, 1993

Related U.S. Application Data

[62] Division of Ser. No. 886,532, May 20, 1992, Pat. No. 5,260,458, which is a division of Ser. No. 766,611, Sep. 26, 1991, Pat. No. 5,117,054.

[51] Int. Cl.$^6$ .......................................... C07D 231/12
[52] U.S. Cl. ................................................. 548/375.1
[58] Field of Search ..................................... 548/375.1

[56] References Cited

U.S. PATENT DOCUMENTS 4,826,868  5/1989  Watcher et al. ............... 548/375.1
4,898,952  2/1990  Murray et al. ................. 548/375.1

Primary Examiner—Robert W. Ramsuer
Attorney, Agent, or Firm—Ralph R. Palo

[57] ABSTRACT

The invention provides a process for preparing 1,5-diaryl pyrazole anti-inflammatory agents. A 6-aryl-4,6-dioxohexanoic acid is treated with acetic anhydride or acetyl chloride to produce an enol lactone, which is added to methylhydroxylamine to generate the dione hydroxamic acid. This dione hydroxamic acid is then treated with 4-methoxyphenylhydrazine hydrochloride to yield the 1,5-diaryl pyrazole. Novel intermediate compounds in the synthetic pathway are also disclosed.

4 Claims, No Drawings

REGIOSELECTIVE SYNTHESIS OF 1,5-DIARYL PYRAZOLE ANTI-INFLAMMATORY AGENTS

This is a division of application Ser. No. 886,532, filed May 20, 1992, now U.S. Pat. No. 5,260,458 which is hereby incorporated by reference, which application is a divisional of application Ser. No. 766,611, filed Sep. 26, 1991, now U.S. Pat. No. 5,117,054.

BACKGROUND OF THE INVENTION

The standard synthesis for pyrazoles involves the reaction of a βeta-dicarbonyl compound with a hydrazine under mild conditions. See A. R. Katritzky in "The Principles of Heterocyclic Chemistry", Academic Press, New York (1968) at page 139. When the hydrazine is mono-substituted and the substituents attached to the two carbonyls of the β-dicarbonyl compound are not equivalent, two isomeric products are possible. While the 1,5-diphenyl pyrazoles have excellent activity in alleviating inflammation and inhibiting the cyclooxygenase and/or lipoxygenase pathways of the arachidonic acid cascade, the 1,3-diphenyl pyrazoles do not show such excellent activity.

A synthetic scheme was developed whereby a high degree of regio-selectivity can be achieved in the preparation of 1,5-diarylpyrazoles. To minimize the production of the undesired isomer, the mono-substituted hydrazine was combined with a β-dicarbonyl compound bearing an aliphatic or aromatic side chain containing a carboxylic acid moiety. This scheme is described in Murray, W., et al., *Synthesis*, 18–20 (January 1991) and U.S. Pat. No. 4,898,952.

Tepoxalin, 3-[5-(4-chlorophenyl)-1-(4-methoxyphenyl)-3-pyrazolyl]-N-hydroxy-N-methylpropanamide, is a potent inhibitor of both the cyclooxygenase and lipoxygenase pathways of the arachidonic acid cascade. Wachter, M. et al, U.S. Pat. No. 4,826,868 (1989) and Robinson, C., *Drugs of the Future*, 15, 9, 202 (1990). One method of synthesizing tepoxalin, is disclosed in U.S. Pat. No. 4,898,952. This process uses methylene chloride and oxalyl chloride in the synthesis. Due to cost and toxicity considerations it is desirable to be able to synthesize tepoxalin without using methylene chloride or oxalyl chloride in the last step of the process. The removal of these reagents from the last step is more important than in earlier steps because earlier purifications and manipulations will dilute and remove traces of these compounds from the reaction stream before they reach the final product if they are used in the last step, the final purification must remove all traces of these materials. The synthesis of structure II described in this invention obviates the need to use oxalyl chloride. The generation of structure II also eliminates the need to use methylene chloride in the last step replacing it with a less toxic alcoholic solvent.

SUMMARY OF THE INVENTION

Accordingly, the present invention provides a process for producing certain 1,5-diaryl pyrazoles without using oxalyl chloride at all and without using methylene chloride in the last step of the synthesis. As a result, toxicity concerns are substantially eliminated. The invention also provides novel intermediate compounds useful in the synthesis of the 1,5-diaryl pyrazoles. The invention further provides a process for producing these novel intermediates.

DETAILED DESCRIPTION OF THE INVENTION

More particularly, the present invention is directed to a process for preparing a compound of the following formula IV:

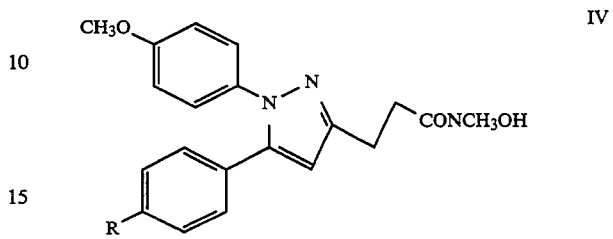

wherein R is either Cl or $CH_3$, according to the following general synthetic scheme:

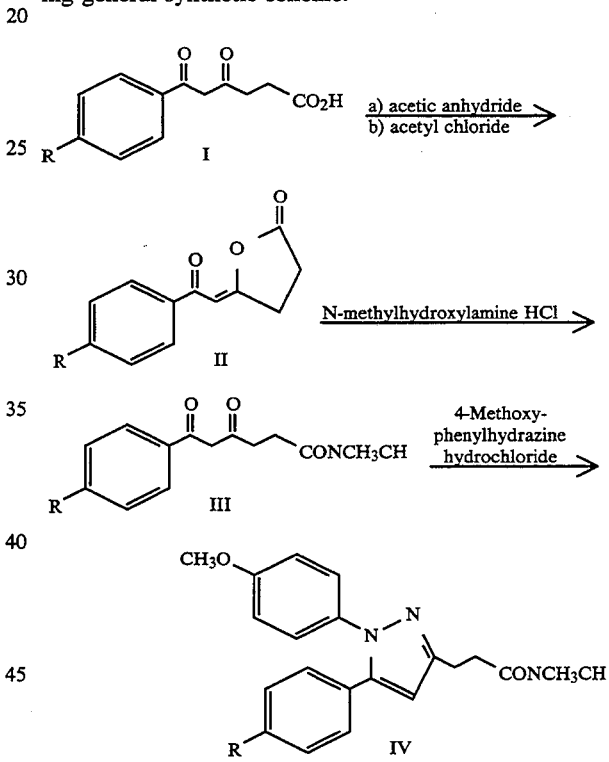

The starting 6-aryl-4,6-dioxohexanoic acids of formula I, 6-(4-chlorophenyl)-4,6-dioxohexanoic acid or 6-(4-methylphenyl)-4,6-dioxohexanoic acid, may be synthesized using the procedures described in Murray, W., *J. Org. Chem.*, 55, 3424 (1990), by acylating the anion of an appropriate acetophenone with succinic anhydride. In the first step of the synthesis, the starting 6-aryl-4,6-dioxohexanoic acid is treated with either acetic anhydride or acetyl chloride and heated at a temperature of about 50° C. to reflux and preferably held at reflux for about 5 to 60 minutes. Thereafter, the acetic anhydride or acetyl chloride is removed in vacuo and the resulting product of formula II is crystallized using a suitable solvent or solvent pair such as ether or hexane/methylene chloride. The compound of formula II is then added slowly to a mixture of N-methylhydroxylamine hydrochloride, an amine base such as triethylamine, Hunig's base, pyridine, or lutidine or other suitable amine bases and a suitable solvent such as methylene chloride or chloroform. The amine base is needed to generate N-methylhydroxylamine which is the reactive species. This reaction is carded out at a temperature of from about −10° to 20° C., and preferably at about 0° C.

After the addition of the compound of formula II is complete, the mixture is preferably stirred for about 1 to 6 hours and allowed to warm to about room temperature. The mixture is then preferably divided into layers by the addition of an acid such as aqueous HCl or dilute aqueous sulfuric acid and the layers are separated. The solvent layer is preferably washed with an acid such as HCl (one or more times), then washed with brine (one or more times), before the solvent layer is dried, preferably over $Na_2SO_4$, filtered and concentrated in vacuo. The resulting compound of formula III is then preferably crystallized using a suitable solvent or solvent pair such as methylene chloride/hexane, ether or ethyl acetate.

The compound of formula III is then combined with 4-methoxyphenylhydrazine hydrochloride, an amine base such as those described previously, and a suitable alcoholic solvent such as methanol, ethanol or propanol. The resulting mixture is then preferably stirred and heated at a temperature of about 50° C. to reflux for about 1 to 24 hours, more preferably 3 to 8 hours. The mixture is then preferably cooled to about room temperature and concentrated in vacuo to a residue. The residue is partitioned between a suitable solvent in ether or ethyl acetate and water. The organic layer is then separated, preferably washed with a suitable acid (one or more times), dried, filtered and thereafter concentrated to a residue. Finally, the resultant product of formula IV is crystallized using a suitable solvent or solvent pair such as ethyl acetate/hexane, ether, or ether/hexane.

When the starting compound is 6-(4-methylphenyl)-4,6-dioxohexanoic acid, the first step of the synthesis yields the novel compound of formula II where R is $CH_3$, 5-[1-(4-methylphenyl)-1-oxo-1-ethanyl-2-ylidene]-2-oxo-2,3,4,5-tetrahydrofuran. The second step yields the novel compound of formula III where R is $CH_3$, 6-(4-methylphenyl)-4,6-dioxo-N-hydroxy-N-methyl-propanamide. The final step yields 3-[5-(4-methylphenyl)-1-(4-methoxyphenyl)-3-pyrazoloyl]-N-hydroxy-N-methylpropanamide.

When the starting compound is 6-(4-chlorophenyl)-4,6-dioxohexanoic acid, the first step of the synthesis yields the novel compound of formula II where R is Cl, 5-[1-(4-chlorphenyl)-1-oxo-1-ethanyl-2-ylidene]-2-oxo-2,3,4,5-tetrahydrofuran. The second step yields the novel compound of formula III where R is Cl, 6-(4-chlorophenyl)-4,6-dioxo-N-hydroxy-N-methylpropanamide. The final step yields tepoxalin, 3-[5-(4-chlorophenyl)-1-(4-methoxyphenyl)-3-pyrazolyl]-N-hydroxy-N-methylpropanamide.

The present invention is also directed to novel intermediate compounds of formulas II and III, which are useful in producing the desired compound of formula IV.

In each of the experimental examples which follow, melting points were determined on a Thomas-Hoover apparatus and are uncorrected. The infrared spectra (IR) were recorded on a Beckman Instruments IR-B spectrophotometer and are expressed in reciprocal centimeters. Nuclear magnetic resonance (NMR) spectra for hydrogen atoms were measured in the indicated solvent with tetramethylsilane (TMS) as the internal standard on a GE QE 300 or an IBM WP-100 spectrometer. The values are expressed in parts per million downfield from TMS. Direct chemical ionization (DCI), mass spectra were obtained on a Finnigan MAT 8230 Double Focusing high resolution mass spectrometer.

EXAMPLE 1

Synthesis of 5-[1 -(4-chlorophenyl)-1 -oxo-1 -ethanyl-2-ylidene]-2-oxo-2,3,4,5-tetrahydrofuran (Step 1)

The compound of formula I where R is Cl was synthesized according to the procedures described in Murray, W. et al *J. Org. Chem.*, 55, 3424 (1990). The compound of formula II where R is Cl was synthesized by suspending 2.54 g of the compound of formula I, 0.01 mol, in 40 mL of acetic anhydride. The mixture was heated to reflux and held there for 20 minutes. At this point, the solution began to darken. The acetic anhydride was removed in vacuo and the brown residue was crystallized from methylene chlodde/hexane to yield 1.92 g (81%) of tan needles, mp 150°–151° C. TLC in hexane/40% EtOAc showed a single compound having the following characteristics:

Anal. Calc'd for $C_{12}H_9ClO_3$ C, 60.90; H, 3.84 Found C, 60.66; H, 3.79

MS (DCl): m/z=237 (M+H), IR (KBr): 1827 $cm^{-1}$, 1686 $cm^{-1}$, 1596 $cm^{-1}$, $^1H$ NMR (DMSO d6) 2.8 (t, 2H, J=8 Hz), 3.5 (t, 2H, J=8 Hz), 6.9 (s, 1H), 7.4 (d, 2H, J=8 Hz), 8.0 (d, 2H, J=8 Hz).

EXAMPLE 2

Synthesis of 6-(4-Chlorophenyl)-4,6-dioxo-N-hydroxy-N-methylpropanamide (Step 2)

The compound of formula III where R is Cl was prepared by dissolving (2.36 g, 0.01 mol), of the compound of formula II from step 1, in $CH_2Cl_2$ (40 mL) and adding the solution dropwise to a mixture of N-methylhydroxylamine hydrochloride (1.28 g, 0.015 mol) and $Et_3N$ (1.5 g, 0.015)in $CH_2Cl_2$ (60 mL) at 0° C. After the addition was complete, the mixture was allowed to warm to room temperature. The mixture was then stirred at room temperature for 2 hours. 20 mL of 10% HCl was added to the mixture and the layers were separated. The $CH_2Cl_2$ layer was washed once with a 20 ml portion of 10% HCl and once with a 20 mL portion of brine. The solvent layer was dried over $Na_2SO_4$, filtered and concentrated in vacuo to yield a yellow solid which was crystallized from $CH_2Cl_2$/hexane to afford 1.96 g (69%) of a yellow solid, mp 135°–137° C., with the following characteristics:

Anal. Calc'd for $C_{13}H_{14}ClNO_4$ C, 55.03; H, 4.98; N, 4.94 Found C, 55.06; H, 5.21; N, 4.82

MS (DCI): m/z=284 (M+H), IR (KBr): 3163 $cm^{-1}$, 1607 $cm^{-1}$, 1591 $cm^{-1}$, $^1H$ NMR (DMSO d6) 2.7 (s, 4H), 3.1 (s, 3H), 6.2 (s, 1H), 7.4 (d, 2H, J=8 Hz), 7.8 (d, 2H, J=8 Hz), 9.5 (br s, 1H).

EXAMPLE 3

Synthesis of 3-[5-(4-Chlorophenyl)-1-(4-methoxyphenyl)-3-pyrazolyl]-N-hydroxy-N-methylpropanamide (step 3)

Tepoxalin, having the formula IV where R is Cl, was prepared according to the following scheme: Compound III from step 2 (1.42 g, 5 mmol), 4-methoxyphenylhydrazine hydrochloride (0.96 g, 5.5 mmol) and Et₃N (0.8 mL, 5.5 mmol) were combined and stirred in methanol (100 mL) at reflux for 6 h. The mixture was cooled and concentrated in vacuo and partitioned between water (50 mL) and ether (100mL). The ether layer was washed with 5% HCl, 2% NaCO₃ and brine, dried over Na₂SO₄, filtered and concentrated to a tan oil which was chromatographed on silica gel and crystallized from EtOAc/hexane to afford 1.22 g (62%) of a white solid, mp 124°–126° C.

Anal. Calc'd for $C_{20}H_{20}ClN_3O_3$ C, 62.26; H, 5.22; N, 10.89 Found C, 62.44; H, 5.20; N, 10.99

MS (DCI): m/z=386 (M+H), IR (KBr) 3150 cm⁻¹, 1660 cm⁻¹, ¹H NMR (CDCl₃) 2.7–3.5 (m, 4H), 3.2 (s, 3H), 3.8 (s, 3H), 6.3 (s, 1H), 6.7–7.4 (m, 8H), 10.7 (br s, 1H).

What is claimed is:

1. A process for preparing a compound of formula IV:

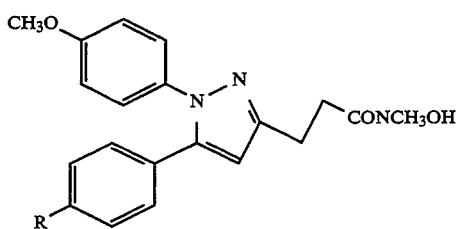

wherein R is selected from either of Cl or CH₃, comprising:

i) reacting a compound of the formula I:

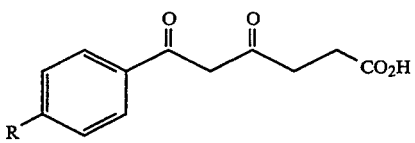

with either of acetic anydride or acetyl chloride to produce a compound of formula II:

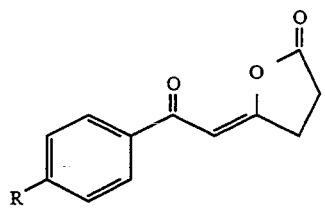

ii) reacting the compound of formula II with N-methylhydroxylamine hydrochloride in the presence of an amine base to produce a compound of formula III:

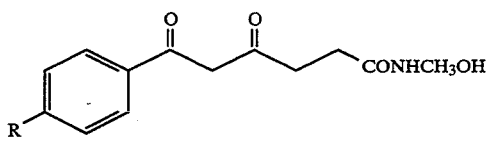

iii) reacting the compound of formula III with 4-methoxyphenylhydrazine hydrochloride in the presence of an amine base to produce the compound of formula IV.

2. The process according to claim 1, wherein the amine base is triethylamine.

3. The process according to claim 2, wherein step (ii) is carried out in the presence of a solvent.

4. The process of claim 2, wherein step (iii) is carried out in the presence of a solvent.

* * * * *